(12) United States Patent
Kumar et al.

(10) Patent No.: US 8,624,041 B2
(45) Date of Patent: Jan. 7, 2014

(54) PROCESS FOR THE PREPARATION OF STRONTIUM RANELATE

(75) Inventors: Bobba Venkata Siva Kumar, Navi Mumbai (IN); Kosampally Srinivas, Navi Mumbai (IN); Sanjay Anantha Kale, Navi Mumbai (IN); Nitin Sharad Chandra Pradhan, Thane (IN)

(73) Assignee: Glenmark Generics Ltd., Mumbai (IN)

( * ) Notice: Subject to any disclaimer, the term of this patent is extended or adjusted under 35 U.S.C. 154(b) by 1082 days.

(21) Appl. No.: 11/990,682

(22) PCT Filed: Aug. 18, 2006

(86) PCT No.: PCT/IB2006/002247
§ 371 (c)(1),
(2), (4) Date: Mar. 23, 2009

(87) PCT Pub. No.: WO2007/020527
PCT Pub. Date: Feb. 22, 2007

(65) Prior Publication Data
US 2009/0214631 A1    Aug. 27, 2009

Related U.S. Application Data

(60) Provisional application No. 60/723,593, filed on Oct. 4, 2005.

(30) Foreign Application Priority Data
Aug. 19, 2005 (IN) ............................. 977/MUM/2005

(51) Int. Cl.
*C07D 333/38* (2006.01)
*A61K 31/381* (2006.01)

(52) U.S. Cl.
USPC ............................................ 549/61; 514/447

(58) Field of Classification Search
USPC ............................................ 514/447; 549/61
See application file for complete search history.

(56) References Cited

U.S. PATENT DOCUMENTS

| 5,128,367 | A | 7/1992 | Wierzbicki et al. | |
| 7,214,805 | B2 * | 5/2007 | Vaysse-Ludot et al. | ........ 549/61 |
| 2004/0063972 | A1 * | 4/2004 | Vaysse-Ludot et al. | ........ 549/61 |

FOREIGN PATENT DOCUMENTS

| EP | 1 403 266 | 3/2004 |
| WO | WO 2004/098619 | 11/2004 |

OTHER PUBLICATIONS

Meunier, P. J., et al., The effects of strontium ranelate on the risk of vertebral fracture in women with postmenopausal osteoprosis, 2004, New England Journal of Medicine, 350;5, pp. 459-468.*
Hultin, P.G., A guide to solvents and reagents in introducory organic chemistry for students in 2.222, 2002, University of Manitoba, Department of Chemistry, (20 pages).*
Gilman, H., et al., Some metalatin Reactions in Tetrahydrofuran, 1958, The Journal of Organic Chemistry, 23(10), cover and pp. 1476-1479 (5 pages).*
Cotton F. A., et al., Advanced Inorganic Chemistry, A Comprehensive Text, 1972, John Wiley & Sons, Inc., Third Edition, 2 cover pages and pp. 189-200.*
Douglas, B.E., et al., Diagonal relationships—the anomalous behaviour or lithium, 1994, Concepts and Models of Inorganic Chemistry, Third Ed., India edition pp. 716 (4 pages).*
Banerjee, D., et al., Recent Advances in s-Block metal carboxylate networks, 2011, Chemical Growth and Design, vol. 11, pp. 4704-4720.*
Atkins et al., The atypical properties of lithium, 2010, Shriver & Atkins' Inorganic Chemistry, Fifth ed., India Ed., pp. 260 & 296, (6 pages).*

* cited by examiner

*Primary Examiner* — Yate K Cutliff
(74) *Attorney, Agent, or Firm* — M. Carmen & Associates, PLLC

(57) ABSTRACT

A process for the preparation of strontium ranelate or a hydrate thereof is provided comprising (a) reacting a tetraester compound of Formula II: wherein R, $R_1$, $R_2$, and $R_3$ are independently a linear or branched $C_1$-$C_6$ alkyl group or a substituted or unsubstituted $C_3$-$C_{12}$ cyclic group, in the presence of a lithium base and in a solvent with an inorganic acid salt of strontium.

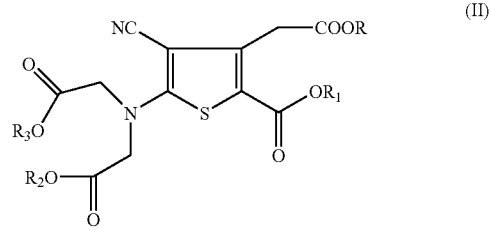

(II)

14 Claims, No Drawings

PROCESS FOR THE PREPARATION OF STRONTIUM RANELATE

PRIORITY

This application claims [the benefit under 35 U.S.C. §119] priority under 35 U.S.C. §371 to International Application No. PCT/IB2006/002247, filed Aug. 18, 2006 and entitled "PROCESS FOR THE PREPARATION OF STRONTIUM RANELATE", which claims priority to U.S. Provisional Application No. 60/723,593, filed on Oct. 4, 2005, and entitled "PROCESS FOR INDUSTRIAL SYNTHESIS OF STRONTIUM RANELATE", and to Indian Provisional Application No. 977/MUM/2005, filed Aug. 19, 2005, and entitled "PROCESS FOR INDUSTRIAL SYNTHESIS OF STRONTIUM RANELATE AND ITS HYDRATES THEREOF", the contents of each of which are incorporated by reference herein.

BACKGROUND OF THE INVENTION

1. Technical Field

The present invention generally relates to an improved process for preparing strontium ranelate and its hydrates.

2. Description of the Related Art

Strontium ranelate, the distrontium salt of 5-[bis(carboxymethyl)amino]-3-carboxymethyl-4-cyano-2-thiophenecarboxylic acid, is represented by the structure of Formula I.

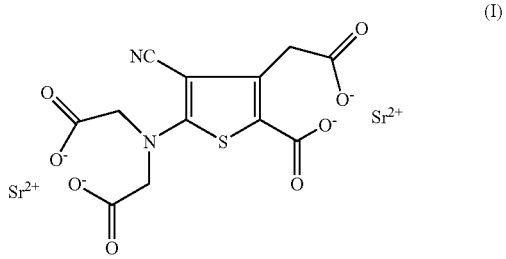

Strontium ranelate has very valuable pharmacological and therapeutic properties, especially pronounced anti-osteoporotic properties, making this compound useful in the treatment of bone diseases.

EP 0415850 and related U.S. Pat. No. 5,128,367 ("the '367 patent") disclose divalent metal salts of 2-[N,N-di(carboxymethyl)amino]-3-cyano4-carboxymethylthiophene-5-carboxylic acid such as strontium ranelate and its tetrahydrate, heptahydrate and octahydrate. The '367 patent further discloses the synthesis of strontium ranelate from the tetraester compound of Formula II:

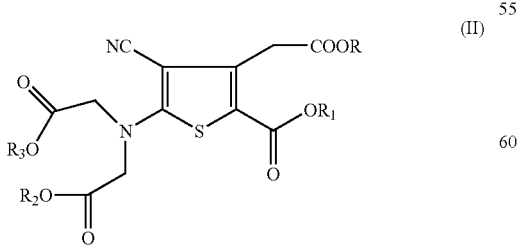

wherein the process involves heating the tetraester compound of Formula II at reflux in an aqueous alcoholic medium in the presence of a sodium hydroxide solution and then hydrolyzing the heated solution in an acidic medium to provide an acid of Formula IV.

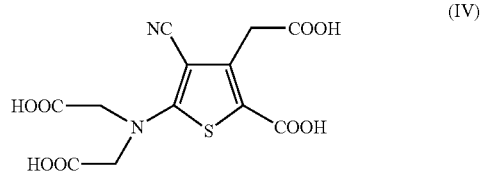

The acid of Formula IV is thereafter converted into its sodium salt and then converted into strontium ranelate using strontium hydroxide or strontium chloride in water.

Another process for preparing strontium ranelate disclosed in the '367 patent includes heating the tetraester compound of Formula II at reflux in a 50/50 mixture by volume of a normal sodium hydroxide solution and ethanol, distilling off the solvents to obtain the tetrasodium salt which is thereafter treated with an aqueous chloride solution of, for example, strontium dichloride.

Yet another process for preparing strontium ranelate disclosed in the '367 patent includes heating the tetraester compound of Formula II at reflux in an aqueous alcoholic medium with a hydroxide, for example, strontium hydroxide. The process disclosed in the '367 patent requires heating at higher temperature, which is believed to generate impurities.

However, industrial production of a compound such as strontium ranelate requires a detailed study of all the reaction steps and of the selection of the starting material reagents and solvents in order to obtain an optimum yield and purity.

Accordingly, there remains a need for a simple industrial process for preparing strontium ranelate and its hydrates in relatively high purity and yield on a commercial scale in a convenient and cost efficient manner. Additionally, it would be desirable to provide a process for preparing strontium ranelate and its hydrates in a shorter reaction time and under mild reaction conditions in which the isolation of the free acid or sodium salt intermediates are completely avoided.

SUMMARY OF THE INVENTION

In accordance with one embodiment of the present invention, a process for the preparation of strontium ranelate or a hydrate thereof is provided comprising reacting a tetraester compound of Formula II:

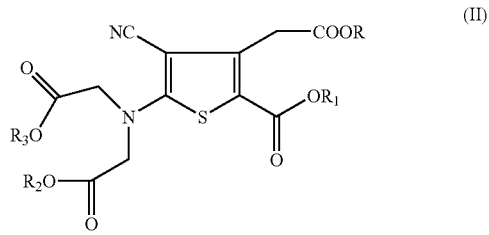

wherein R, $R_1$, $R_2$, and $R_3$ are independently a linear or branched $C_1$-$C_6$ alkyl group or a substituted or unsubstituted $C_3$-$C_{12}$ cyclic group, in the presence of a lithium base and in a solvent with an inorganic acid salt of strontium.

In accordance with a second embodiment of the present invention, a lithium salt is provided having the structure of Formula III.

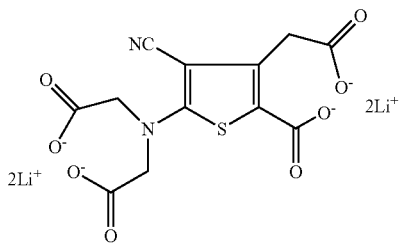

(III)

In accordance with a third embodiment of the present invention, strontium ranelate or a hydrate thereof having a purity greater than or equal to about 99% is provided.

In accordance with a fourth embodiment of the present invention, a pharmaceutical composition is provided comprising a therapeutically effective amount of strontium ranelate or a hydrate thereof having a purity greater than or equal to about 99%.

Definitions

The term "HPLC" as used herein means high performance liquid chromatograpy.

The term "treating" or "treatment" of a state, disorder or condition as used herein means: (1) preventing or delaying the appearance of clinical symptoms of the state, disorder or condition developing in a mammal that may be afflicted with or predisposed to the state, disorder or condition but does not yet experience or display clinical or subclinical symptoms of the state, disorder or condition, (2) inhibiting the state, disorder or condition, i.e., arresting or reducing the development of the disease or at least one clinical or subclinical symptom thereof, or (3) relieving the disease, i.e., causing regression of the state, disorder or condition or at least one of its clinical or subclinical symptoms. The benefit to a subject to be treated is either statistically significant or at least perceptible to the patient or to the physician.

The term "therapeutically effective amount" as used herein means the amount of a compound that, when administered to a mammal for treating a state, disorder or condition, is sufficient to effect such treatment. The "therapeutically effective amount" will vary depending on the compound, the disease and its severity and the age, weight, physical condition and responsiveness of the mammal to be treated.

The term "delivering" as used herein means providing a therapeutically effective amount of an active ingredient to a particular location within a host means causing a therapeutically effective blood concentration of the active ingredient at the particular location. This can be accomplished, e.g., by topical, local or by systemic administration of the active ingredient to the host.

The term "buffering agent" as used herein means a compound used to resist a change in pH upon dilution or addition of acid of alkali. Such compounds include, by way of example and without limitation, potassium metaphosphate, potassium phosphate, monobasic sodium acetate and sodium citrate anhydrous and dehydrate and other such material known to those of ordinary skill in the art.

The term "sweetening agent" as used herein means a compound used to impart sweetness to a preparation. Such compounds include, by way of example and without limitation, aspartame, dextrose, glycerin, mannitol, saccharin sodium, sorbitol, sucrose, fructose and other such materials known to those of ordinary skill in the art.

The term "binders" as used herein means substances used to cause adhesion of powder particles in tablet granulations. Such compounds include, by way of example and without limitation, acacia alginic acid, tragacanth, carboxymethylcellulose sodium, poly (vinylpyrrolidone), compressible sugar (e.g., NuTab), ethylcellulose, gelatin, liquid glucose, methylcellulose, povidone and pregelatinized starch, combinations thereof and other material known to those of ordinary skill in the art.

When needed, other binders may also be included in the present invention. Exemplary binders include starch, poly (ethylene glycol), guar gum, polysaccharide, bentonites, sugars, invert sugars, poloxamers (PLURONIC™ F68, PLURONIC™ F127), collagen, albumin, celluloses in nonaqueous solvents, combinations thereof and the like. Other binders include, for example, poly(propylene glycol), polyoxyethylene-polypropylene copolymer, polyethylene ester, polyethylene sorbitan ester, poly(ethylene oxide), microcrystalline cellulose, poly(vinylpyrrolidone), combinations thereof and other such materials known to those of ordinary skill in the art.

The term "diluent" or "filler" as used herein means inert substances used as fillers to create the desired bulk, flow properties, and compression characteristics in the preparation of tablets and capsules. Such compounds include, by way of example and without limitation, dibasic calcium phosphate, kaolin, sucrose, mannitol, microcrystalline cellulose, powdered cellulose, precipitated calcium carbonate, sorbitol, starch, combinations thereof and other such materials known to those of ordinary skill in the art.

The term "glidant" as used herein means agents used in tablet and capsule formulations to improve flow-properties during tablet compression and to produce an anti-caking effect. Such compounds include, by way of example and without limitation, colloidal silica, calcium silicate, magnesium silicate, silicon hydrogel, cornstarch, talc, combinations thereof and other such materials known to those of ordinary skill in the art.

The term "lubricant" as used herein means substances used in tablet formulations to reduce friction during tablet compression. Such compounds include, by way of example and without limitation, calcium stearate, magnesium stearate, mineral oil, stearic acid, zinc stearate, combinations thereof and other such materials known to those of ordinary skill in the art.

The term "disintegrant" as used herein means a compound used in solid dosage forms to promote the disruption of the solid mass into smaller particles which are more readily dispersed or dissolved. Exemplary disintegrants include, by way of example and without limitation, starches such as corn starch, potato starch, pre-gelatinized and modified starched thereof, sweeteners, clays, such as bentonite, microcrystalline cellulose (e.g. Avicel™), carsium (e.g. Amberlite™), alginates, sodium starch glycolate, gums such as agar, guar, locust bean, karaya, pectin, tragacanth, combinations thereof and other such materials known to those of ordinary skill in the art.

The term "wetting agent" as used herein means a compound used to aid in attaining intimate contact between solid particles and liquids. Exemplary wetting agents include, by way of example and without limitation, gelatin, casein, lecithin (phosphatides), gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters, (e.g., TWEEN™s), polyethylene glycols, polyoxyethylene stearates colloidal silicon dioxide, phosphates, sodium dodecylsulfate, carboxymethylcellulose calcium, carboxymethylcellulose sodium, methylcellulose, hydroxyethylcellulose, hydroxyl propylcellulose, hydroxypropylmethylcellulose phthalate, noncrystalline cellulose, magnesium aluminum silicate, triethanolamine, polyvinyl alcohol, polyvinylpyrrolidone (PVP), tyloxapol (a nonionic liquid polymer of the alkyl aryl polyether alcohol type, also known as superinone or triton), combinations thereof and other such materials known to those of ordinary skill in the art.

Most of these excipients are described in detail in, e.g., Howard C. Ansel et al., Pharmaceutical Dosage Forms and Drug Delivery Systems, (7th Ed. 1999); Alfonso R. Gennaro et al., Remington: The Science and Practice of Pharmacy, (20th Ed. 2000); and A. Kibbe, Handbook of Pharmaceutical Excipients, (3rd Ed. 2000), which are incorporated by reference herein.

DETAILED DESCRIPTION OF THE PREFERRED EMBODIMENTS

The present invention is directed to a process for the preparation of strontium ranelate of Formula I and its hydrates from the tetraester compound of Formula II via formation of a lithium salt of Formula III.

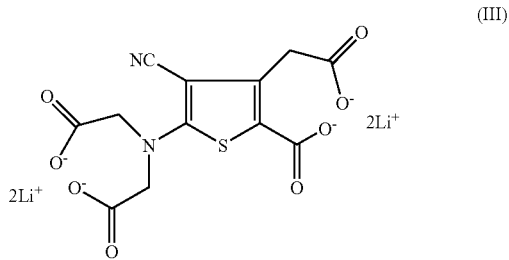

(III)

In one embodiment, a process of the present invention includes at least reacting a tetraester compound of Formula II in the presence of a lithium base and in a solvent with an inorganic acid salt of strontium and optionally (b) isolating the strontium ranelate or a hydrate thereof.

The starting tetraester compound for use in step (a) of the process of the present invention is represented by the structure of Formula II:

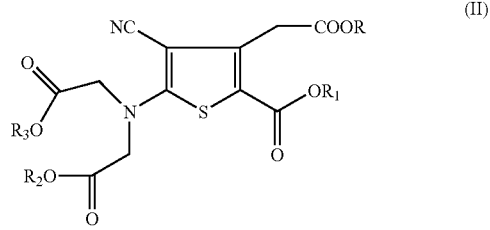

(II)

wherein R, $R_1$, $R_2$ and $R_3$ are independently a linear or branched $C_1$-$C_6$ alkyl group or a substituted or unsubstituted $C_3$-$C_{12}$ cyclic group. Representative examples of alkyl groups for use herein include, by way of example, a straight or branched hydrocarbon chain radical containing carbon and hydrogen atoms of from 1 to about 6 carbon atoms with or without unsaturation, to the rest of the molecule, e.g., methyl, ethyl, n-propyl, n-butyl, n-pentyl, and the like. Representative examples of cyclic groups for use herein include, by way of example, substituted or unsubstituted cyclic radicals containing from 3 to about 12 carbon atoms, e.g., cyclopropyl, cyclobutyl, cyclopentyl, cyclohexyl radicals and the like. The starting tetraester of Formula II is well known and is described in the literature, e.g., M. Wierzbicki et al., Bull. Soc. Chim. pages 1786-1792 (1975). In one embodiment, the staring tetraester is the 5-(bis-ethoxycarbonylmethyl-amino)-4-cyano-3-methoxycarbonylmethyl-thiophene-2-carboxylic acid ethyl ester.

Any lithium base can be used in step (a) of the process of the present invention. A suitable lithium base includes, but is not limited to, lithium hydroxide, lithium carbonate, lithium hydroxide monohydrate and the like and mixtures thereof. If desired, the lithium base can be an aqueous solution containing at least the lithium based. Generally, the lithium base can be present in an amount ranging from about 25% w/w to about 80% w/w and preferably from about 35% w/w to about 65% w/w.

Soluble solvents for use herein include, but are not limited to, alcohols, cyclic ethers, water, ketones, nitrites, and the like and mixture thereof. In one embodiment, the solvent is one or more polar aprotic solvents. Suitable alcohol solvents include $C_1$-$C_{10}$ alcohols such as methanol, ethanol, isopropyl and the like and mixtures thereof. Suitable cyclic ethers include tetrahydrofuran, dioxane and the like and mixture thereof. Suitable ketones can have from 1 to about 20 carbon atoms such as acetone, methyl ethyl ketone, diethyl ketone, methyl propyl ketone, methyl isopropyl ketone, ethyl propyl ketone, ethyl isopropyl ketone, dipropyl ketone, diisopropyl ketone, methyl butyl ketone, methyl isobutyl ketone and the like. Suitable nitrites include, but are not limited to, acetonitrile and the like. The solvent will ordinarily be present in an amount of about 1 to about 10 volumes.

Suitable inorganic acid salts of strontium for use in step (a) of the process of the present invention include, but are not limited to, strontium chloride, strontium nitrate, strontium bromide, strontium sulfate and the like and mixtures thereof. Generally, the amount of the inorganic acid salt of strontium, e.g., strontium chloride, can range from about 1 mole to about 2.5 moles per one mole of the tetraester compound of Formula II.

In general, step (a) of the process of the present invention can be carried out at a suitable temperature and for a sufficient period of time to form the strontium renelate or hydrate thereof. A suitable temperature will ordinarily range from about 0° C. to about 70° C. In another embodiment, the temperature is room temperature. The time period can range from about 15 hours to about 45 hours.

In one embodiment, the preparation of the strontium ranelate or hydrate thereof from the tetraester compound of Formula II can be via formation of a lithium salt of Formula III in situ. For example, the reaction can be carried out by forming a first solution containing at least the tetraester of Formula II, a lithium base and a first solvent such that a lithium salt of Formula III is formed in situ and then adding a second solution containing at least the inorganic acid salt of strontium and a second solvent to form strontium ranelate or a hydrate thereof. The first and second solvents can be any of the aforementioned solvents. In one embodiment, the first and second solvents are the same. In another embodiment, the first and second solvents are different. In another embodiment, the first solvent is an alcohol or cyclic ether and the second solvent is water. When water is employed as a solvent, it is ordinarily added in an amount ranging from about 3 to about 10 volumes.

In another embodiment, the preparation of the strontium ranelate or hydrate thereof from the tetraester compound of Formula II can be carried out by first forming a lithium salt of Formula III; isolating the lithium salt by conventional techniques, e.g., filtration, and then reacting the lithium salt with at least the inorganic acid salt of strontium to form the strontium ranelate or hydrate thereof.

If desired, the strontium ranelate or hydrate thereof thus obtained can then be isolated and recovered. For example, when carrying out the reaction in a solvent which the reactants are relatively more soluble than the strontium ranelate or hydrate thereof, e.g., water, the strontium salt forming reaction will be accompanied by a spontaneous precipitation out of solution of the strontium ranelate or strontium ranelate hydrate. The precipitated strontium ranelate or hydrate thereof can then be recovered by conventional techniques, e.g., filtration or centrifugation, optionally followed by washing and/or drying.

The strontium ranelate and its hydrates thus obtained can be of relatively high purity, e.g., a purity greater than or equal to about 99% and preferably greater than or equal to about 99.5% and in a yield of greater than about 85%, which is reproducible on an industrial scale.

Yet another aspect of the present invention is directed to pharmaceutical compositions containing at least the strontium ranelate or hydrate thereof of the present invention. Such pharmaceutical compositions may be administered to a mammalian patient in any dosage form, e.g., liquid, powder, elixir, injectable solution, etc. Dosage forms may be adapted for administration to the patient by oral, buccal, parenteral, ophthalmic, rectal and transdermal routes or any other acceptable route of administration. Oral dosage forms include, but are not limited to, tablets, pills, capsules, troches, sachets, suspensions, powders, lozenges, elixirs and the like. The strontium ranelate or hydrate thereof of the present invention also may be administered as suppositories, ophthalmic ointments and suspensions, and parenteral suspensions, which are administered by other routes. The dosage forms may contain the strontium ranelate or hydrate thereof of the present invention as is or, alternatively, may contain the strontium ranelate or hydrate thereof as part of a composition. The pharmaceutical compositions may further contain one or more pharmaceutically acceptable excipients. Suitable excipients and the amounts to use may be readily determined by the formulation scientist based upon experience and consideration of standard procedures and reference works in the field, e.g., the buffering agents, sweetening agents, binders, diluents, fillers, lubricants, wetting agents and disintegrants described hereinabove.

Capsule dosages will contain the strontium ranelate or hydrate thereof of the present invention within a capsule which may be coated with gelatin. Tablets and powders may also be coated with an enteric coating. The enteric-coated powder forms may have coatings containing at least phthalic acid cellulose acetate, hydroxypropylmethyl cellulose phthalate, polyvinyl alcohol phthalate, carboxy methyl ethyl cellulose, a copolymer of styrene and maleic acid, a copolymer of methacrylic acid and methyl methacrylate, and like materials, and if desired, they may be employed with suitable plasticizers and/or extending agents. A coated capsule or tablet may have a coating on the surface thereof or may be a capsule or tablet comprising a powder or granules with an enteric-coating.

Tableting compositions may have few or many components depending upon the tableting method used, the release rate desired and other factors. For example, the compositions of the present invention may contain diluents such as cellulose-derived materials like powdered cellulose, microcrystalline cellulose, microfine cellulose, methyl cellulose, ethyl cellulose, hydroxyethyl cellulose, hydroxypropyl cellulose, hydroxypropylmethyl cellulose, carboxymethyl cellulose salts and other substituted and unsubstituted celluloses; starch; pregelatinized starch; inorganic diluents such calcium carbonate and calcium diphosphate and other diluents known to one of ordinary skill in the art. Yet other suitable diluents include waxes, sugars (e.g. lactose) and sugar alcohols like mannitol and sorbitol, acrylate polymers and copolymers, as well as pectin, dextrin and gelatin.

Other excipients contemplated by the present invention include binders, such as acacia gum, pregelatinized starch, sodium alginate, glucose and other binders used in wet and dry granulation and direct compression tableting processes; disintegrants such as sodium starch glycolate, crospovidone, low-substituted hydroxypropyl cellulose and others; lubricants like magnesium and calcium stearate and sodium stearyl fumarate; flavorings; sweeteners; preservatives; pharmaceutically acceptable dyes and glidants such as silicon dioxide.

In one embodiment, the strontium ranelate or hydrate thereof disclosed herein for use in the pharmaceutical compositions of the present invention can have a $D_{50}$ and $D_{90}$ particle size of less than about 400 microns, preferably less than about 200 microns, more preferably less than about 150 microns, still more preferably less than about 50 microns and most preferably less than about 15 microns. The term "micronization" used herein means any process or methods by which the size of the particles is reduced. For example, the particle sizes of the strontium ranelate or hydrate thereof can be obtained by any milling, grinding, micronizing or other particle size reduction method known in the art to bring the solid state form of the strontium ranelate or hydrate thereof of the present invention into any of the foregoing desired particle size range. As also used herein, strontium ranelate or hydrate thereof particles with reduced size are referred to as "micronized particles of strontium ranelate or hydrate thereof" or "micronized strontium ranelate or hydrate thereof".

Actual dosage levels of the strontium ranelate or hydrate thereof in the compositions of the invention may be varied to obtain an amount of strontium ranelate or hydrate thereof that is effective to obtain a desired therapeutic response for a particular composition and method of administration. The selected dosage level therefore depends upon such factors as, for example, the desired therapeutic effect, the route of administration, the desired duration of treatment, and other factors. The total daily dose of the compounds of this invention administered to a host in single or divided dose and can vary widely depending upon a variety of factors including, for example, the body weight, general health, sex, diet, time and route of administration, rates of absorption and excretion, combination with other drugs, the severity of the particular condition being treated, etc.

The strontium ranelate or hydrate thereof disclosed herein for use in the pharmaceutical compositions of the present invention is particularly useful in the treatment of a bone disease or condition such as, for example, osteoporosis, osteoarthritis, osteopetrosis, osteopenia and Paget's disease, hypercalcemia of malignancy, periarticular erosions in rheumatoid arthritis, osteodystrophy, myositis ossificans, Bechterew's disease, malignant hypercalcemia, osteolytic lesions produced by bone metastasis, bone loss due to sex steroid hormone deficiency, bone abnormalities due to steroid hormone treatment, bone abnormalities caused by cancer therapeutics, osteomalacia, Bechet's disease, hyperostosis, metastatic bone disease, immobilization-induced osteopenia or osteoporosis, or glucocorticoid-induced osteopenia or osteoporosis, osteoporosis pseudoglioma syndrome, idiopathic juvenile osteoporosis, and for the improvement of fracture healing after traumatic or atraumatic fracture.

The following examples are provided to enable one skilled in the art to practice the invention and are merely illustrative of the invention. The examples should not be read as limiting the scope of the invention as defined in the features and advantages.

EXPERIMENTAL

The purity was compounds of the examples was measured by high performance liquid chromatography (HPLC) under the following conditions: Column $C_{18}$ Inertsil ODS 3V, 250× 4.6 mm, 5 µ (GL Sciences Inc.; Japan)

| Mobile Phase: | |
| --- | --- |
| Mobile Phase: | Methanol (80:20, v/v) A = Buffer: |
| Mobile Phase: | Methanol (25:75, v/v) B = Buffer: |
| Buffer: | 0.05M Potassium dihydrogen phosphate in water. Adjust pH to 3.0 with ortho phosphoric acid. |

| Time | % Mobile phase A | % Mobile phase B |
| --- | --- | --- |
| 0 | 90 | 10 |
| 15 | 25 | 75 |
| 25 | 10 | 90 |
| 30 | 10 | 90 |
| 35 | 25 | 75 |
| 38 | 25 | 75 |
| 45 | 90 | 10 |
| 50 | 90 | 10 |

| Detector: | UV, 236 nm |
| --- | --- |
| Flow rate: | 0.8 ml/minute |
| Retention time: | about 6.5 minutes |
| Injection Volume: | 10 µl |

EXAMPLE 1

Preparation of distrontium salt of 2-[N-N-di(carboxymethyl-)amino]-3-cyano-4-carboxymethylthiophene-5-carboxylic acid in the form of an octahydrate.

A mixture of tetrahydrofuran (375 ml), 5-(bis-ethoxycarbonylmethyl-amino)-4-cyano-3-methoxycarbonylmethylthiophene-2-carboxylic acid ethyl ester (250 g) and 1200 ml 10% aq. solution of lithium hydroxide was stirred at room temperature for about 4 to 6 hours in a round bottom flask. The reaction mass was filtered off to remove any insoluble material. The clear filtrate was further stirred with 2.2 moles of strontium chloride in 1.7 liters of water for 15 to 20 hours at room temperature. The precipitated solid, distrontium salt of 2-[N-N-di(carboxymethyl-)amino]-3-cyano-4-carboxymethylthiophene-5-carboxylic acid in the form of an octahydrate, was filtered off and washed with water to form a wet cake. The resulting wet cake was dried to yield 333 grams of strontium ranelate octahydrate having a purity greater than 99.5% as determined by HPLC.

EXAMPLE 2

Preparation of a Lithium Salt.

A mixture of tetrahydrofuran (375 ml), 5-(bis-ethoxycarbonylmethyl-amino)-4-cyano-3-methoxycarbonylmethylthiophene-2-carboxylic acid ethyl ester (250 g) and 1200 ml 10% aq. solution of lithium hydroxide monohydrate was stirred at room temperature for about 3 to 4 hours in a round bottom flask. The reaction mass was filtered off to remove any insoluble material. The clear filtrate was further distilled below 55° C. to get oily residue to which 250 ml of toluene was added and further distilled below 55° C. to remove water traces if any to get oily residue. Next, a mixture of methanol and ethyl acetate (2.5 liters; 1:1 mixture) was added to the oily residue and the reaction mass was stirred at 55° C. to get a free solid. The reaction mass was cooled under stirring at room temperature and a precipitate of the lithium salt was formed. The precipitated solid of the lithium salt was filtered off and washed with a mixture of methanol and ethyl acetate (250 ml; 1:1) to form a wet cake. The wet cake was dried to yield 240 grams of the lithium salt.

EXAMPLE 3

Preparation of distrontium salt of 2-[N-N-di(carboxymethyl-)amino]-3-cyano-4-carboxymethylthiophene-5-carboxylic acid in the form of an octahydrate.

Into a round bottom flask was added 240 grams of the lithium salt obtained in Example 2 and water (1200 ml) to form a mixture. The mixture was stirred at room temperature for about 10 to 15 minutes to provide a clear solution. The reaction mass was filtered off to remove any insoluble material. The clear filtrate was further stirred with 2.2 moles of strontium chloride in 1.7 liters of water for 15 to 20 hours at room temperature. The precipitated solid, distrontium salt of 2-[N-N-di(carboxymethyl-)amino]-3-cyano-4-carboxymethylthiophene-5-carboxylic acid in the form of an octahydrate, was filtered off and washed with water to provide a wet cake. The wet cake was dried to yield 316 grams of strontium ranelate octahydrate having a purity greater than 99.5% as determined by HPLC.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the features and advantages appended hereto.

What is claimed is:

1. A process for the preparation of strontium ranelate or a hydrate thereof comprising (a) forming a solution comprising a tetraester compound of Formula II

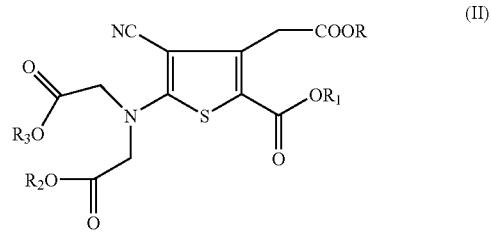

wherein R, $R_1$, $R_2$, and $R_3$ are independently a linear or branched $C_1$-$C_6$ alkyl group or a substituted or unsubstituted $C_3$-$C_{12}$ cyclic group a lithium base and a first solvent such that a lithium salt of Formula III is formed in situ

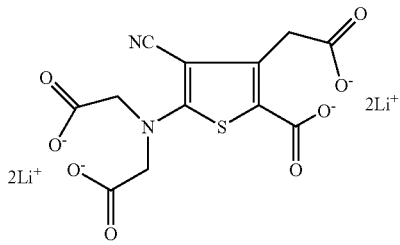

(III)

and then adding a second solution comprising an inorganic acid salt of strontium and a second solvent to form the strontium ranelate or hydrate thereof; wherein the first solvent is a polar aprotic solvent and second solvent is water.

2. The process of claim 1, wherein the lithium base is selected from the group consisting of lithium hydroxide, lithium carbonate, lithium hydroxide monohydrate and mixtures thereof.

3. The process of claim 1, wherein the first solvent is a cyclic ether.

4. The process of claim 1, wherein the inorganic acid salt of strontium is selected from the group consisting of strontium chloride, strontium nitrate, strontium bromide, strontium sulfate and mixtures thereof.

5. The process of claim 1, further comprising precipitating the strontium ranelate or hydrate thereof and recovering the strontium ranelate or hydrate thereof.

6. The process of claim 1, wherein the strontium ranelate or hydrate thereof thus obtained has a purity greater than or equal to about 99.5%.

7. A lithium salt of Formula III:

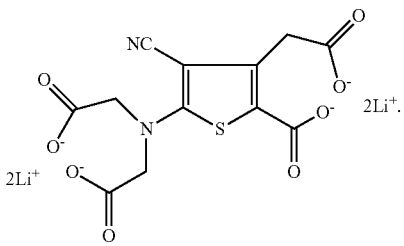

(III)

8. A process for preparing a lithium salt of Formula III:

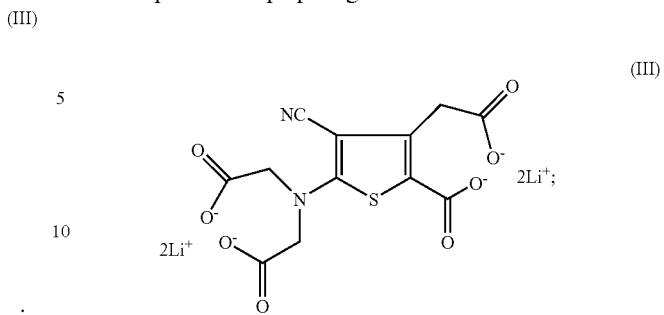

(III)

the process comprising reacting a tetraester compound of Formula II:

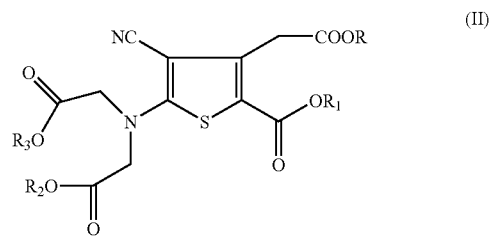

(II)

wherein R, $R_1$, $R_2$, and $R_3$ are independently a linear or branched $C_1$-$C_6$ alkyl group or a substituted or unsubstituted $C_3$-$C_{12}$ cyclic group, with a lithium base and in a polar aprotic solvent.

9. The process of claim 8, wherein the lithium base is lithium hydroxide monohydrate.

10. The process of claim 8, wherein the solvent is a cyclic ether.

11. The process of claim 8, wherein the lithium salt of Formula III is thereafter converted to strontium ranelate octahydrate.

12. The process of claim 1, wherein the polar aprotic solvent is tetrahydrofuran.

13. The process of claim 8, wherein the polar aprotic solvent is tetrahydrofuran.

14. The process of claim 1, further comprising the step of isolating the lithium compound of Formula III prior to adding the second solution.

\* \* \* \* \*